United States Patent [19]

Harrick

[11] Patent Number: 4,602,869
[45] Date of Patent: Jul. 29, 1986

[54] INTERNAL REFLECTION PRISM LIQUID CELL

[76] Inventor: Nicolas J. Harrick, Croton Dam Rd., Ossining, N.Y. 10562

[21] Appl. No.: 557,847

[22] Filed: Dec. 5, 1983

[51] Int. Cl.$^4$ ............................................. G01N 21/16
[52] U.S. Cl. .................................... 346/244; 356/246; 356/440; 356/445
[58] Field of Search ................ 356/244, 246, 440, 445

[56] References Cited

U.S. PATENT DOCUMENTS

| | | | |
|---|---|---|---|
| 3,369,446 | 2/1968 | McCarthy | 356/244 |
| 3,490,847 | 1/1970 | Berz et al. | 356/244 |
| 3,501,241 | 3/1970 | Hansen et al. | 356/244 |
| 3,591,287 | 7/1971 | Hannis | 356/244 |

OTHER PUBLICATIONS

Internal Reflection Spectroscopy by N. J. Harrick, Harrick Scientific Corporation, Ossining, New York 1979.
Industrial Research Development Magazine–"Prism Liquid Cell", vol. 37, Nov. 6, 1983, pp. 573-578.

Primary Examiner—John E. Kittle

[57] ABSTRACT

An internal reflection cell for use in internal reflection spectroscopy comprising a transparent body having at a bottom surface two reflecting mirrors and at a top surface means for mounting of an internal reflection prism element. A sealed cell construction is also described. The cell is intended primarily for analysis of liquid samples.

18 Claims, 8 Drawing Figures

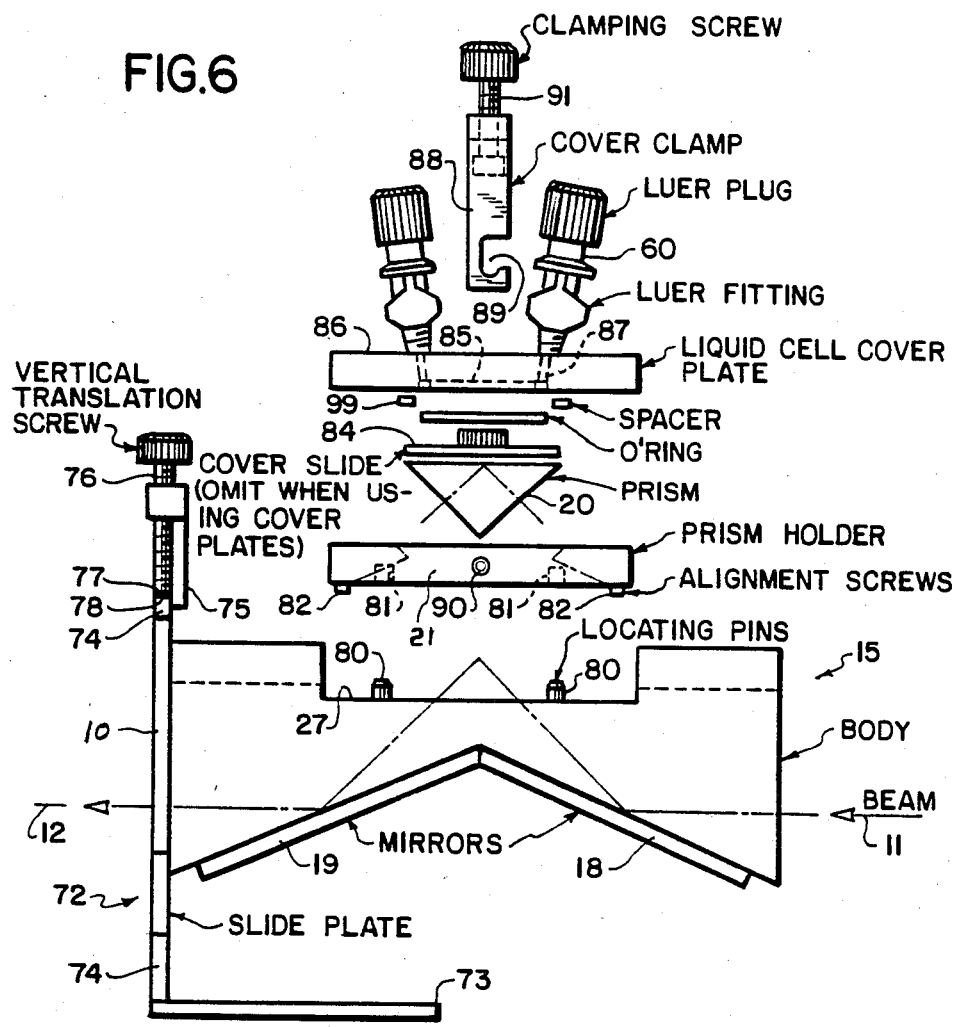
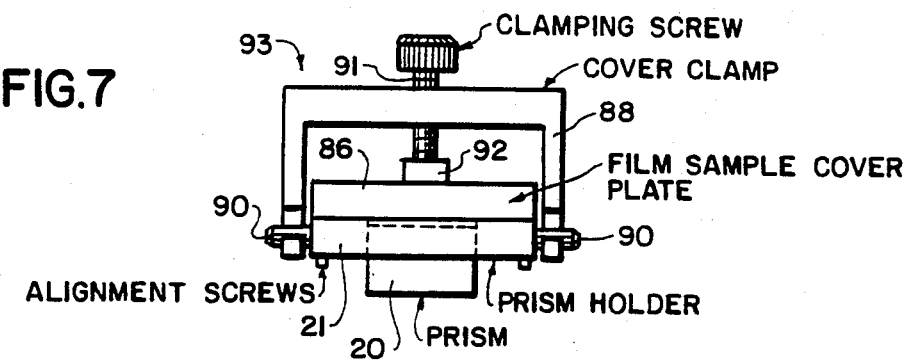

INTERNAL REFLECTION PRISM LIQUID CELL

This invention relates to optical absorption spectroscopy, more particularly, to internal reflection spectroscopy (IRS), and specifically, to an internal reflection prism cell serving as an accessory or attachment for holding or supporting a liquid or other sample for material identification or analysis.

BACKGROUND OF THE INVENTION

The applicant's book entitled "Internal Reflection Spectroscopy", published 1967 by Interscience Publishers (John Wiley & Sons), which is hereby incorporated by reference, describes in detail the development of IRS, its use for material analysis and identification, and includes a detailed description of various kinds of internal reflection elements (IRE) used for establishing the conditions necessary to obtain internal reflection spectra of material samples in solid, liquid or gas phase form. The present invention is directed to a cell attachment primarily for use with liquid samples, that is, a device which includes an IRE for holding a sample and designed to be attached to an existing commercially-available spectrometer for receiving the light beam over a broad spectral range from ultraviolet to the far infrared, direct it into the IRE to the surface supporting the sample, and then redirect the internally reflected attenuated beam back into the spectrometer exactly as it would have entered in the absence of the attachment. The known liquid cells often have shortcomings, such as complexity and general inflexibility. There is a need in the art for a liquid cell for use in IRS characterized by simplicity, minimum components, ease of alignment, precisely mounted mirrors, maintenance of sharp focus, and capable of conducting measurements at room and elevated or reduced temperatures, of thin films, pressurized films, and flow through liquids.

BRIEF DESCRIPTION OF THE INVENTION

A principal object of the invention is an IR prism liquid cell accessory or attachment for IRS characterized by a relatively simple optical geometry and ease of use.

Another object of the invention is an IR prism liquid cell readily adapted for use with liquid samples in a thin film mode, a pressurized film mode, and with liquids in a flow through mode.

Still a further object of the invention is a novel IR prism liquid cell characterized by simplicity, minimum components, ease of alignment, precisely mounted mirrors, maintenance of sharp focus, and capable of multimode use.

These and further objects of the invention are achieved in accordance with one aspect of the invention with an IR cell construction characterized by an optically transparent body having two adjacent mirrors for, respectively, receiving the incident beam and directing it toward an IRE prism cell mounted on the body and receiving the return beam from the prism cell and directing it back into the spectrometer.

In accordance with another aspect of the invention, means are provided to mount the IR prism cell in an accurate optical position on the body which greatly simplifies assembly and disassembly of the structure for, among other reasons, cleaning the sample surface.

In accordance with still another aspect of the invention, means are provided for operating the accessory in a relatively simple manner in multiple modes, more specifically, a thin film mode, a pressurized film mode, and a flow through mode.

DESCRIPTION OF DRAWINGS

Exemplary embodiments of the invention will be described in connection with the annexed drawings, wherein:

FIG. 6 is an exploded detail view, also taken from the side, of still another modification of a cell in accordance with the invention;

FIG. 7 is an end view of an assembled subassembly of part of the FIG. 6 embodiment;

DESCRIPTION OF PREFERRED EMBODIMENTS

Figure 1:
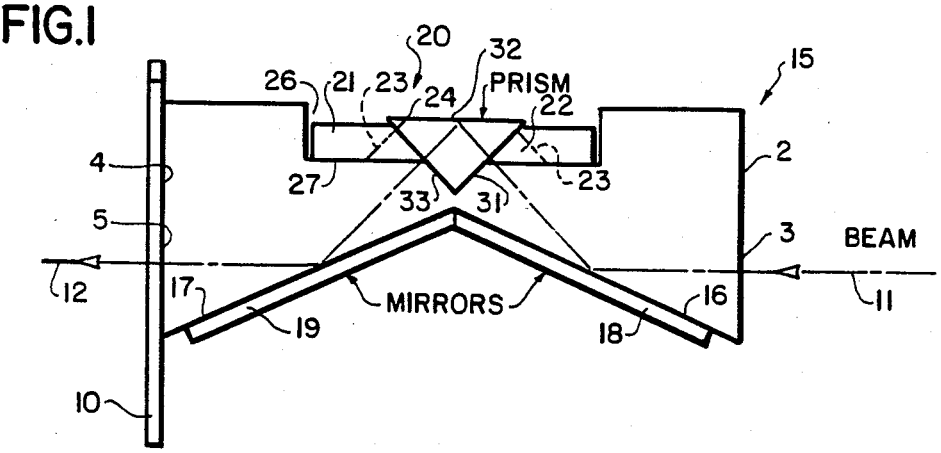
FIG. 1 is a simplified side view of one form of the invention showing the basic construction and optical geometry of a non-sealed cell.

Referring now to FIG. 1 of the drawings, a liquid cell in accordance with the invention comprises, essentially, a support element 10 for supporting the cell on means not shown in the sampling space of a spectrometer (not shown), which typically includes a radiation or light beam generator (ultraviolet through far infrared) (not shown) which supplies an incident light beam 11, which is typically focussed at an entrance slit (not shown), which would be located at the left of the figure, of the spectral analysis unit of the instrument. The beam after interaction with the sample is selectively absorbed and thus attenuated at wavelengths characteristic of the sample material, and thus a plot of optical beam attenuation as a function of wavelength gives information concerning the nature of the sample. The cell shown functions to direct the incident beam 11 to the IRE prism sample holder, and then to redirect the return beam 12 back into the spectrometer for analysis.

The cell shown comprises an optically transparent block 15 having at its right side surface 2 an entrance aperture 3 for the incident beam 11 and at its left side surface 4 an exit aperture 5 for the exiting beam 12, and having at its bottom inverted V-shaped surfaces 16, 17 for mounting, respectively, of first and second plane mirrors 18, 19. At the top is provided means for removably supporting the IRE, in the embodiment shown a simple 45° triangular prism block 20. The mounting means comprises a mounting plate 21 with a central generally rectangular opening 22, whose sides 23 slant outwardly at the bottom and whose upper edge is bevelled at 24. The dimensions are chosen such that the prism 20 with its apex down seats neatly within the opening 22 supported at its sides by the opposed bevelled edges 24. The plate 21 with its supported prism 20 seats within a rectangular recess 26 at a top surface 27 of the block 15. The optical geometry shown is that of a fixed angle, single internal reflection element. As illustrated, the incident beam 11 after reflection from the first mirror 18 enters orthogonally the prism at surface 31, internally reflects once off the top surface 32, which would contain the sample, exits orthogonally via surface 33 of the prism, and after reflection off the second mirror 19 is reoriented along the optical axis of the instrument as exit beam 12.

Figure 2:
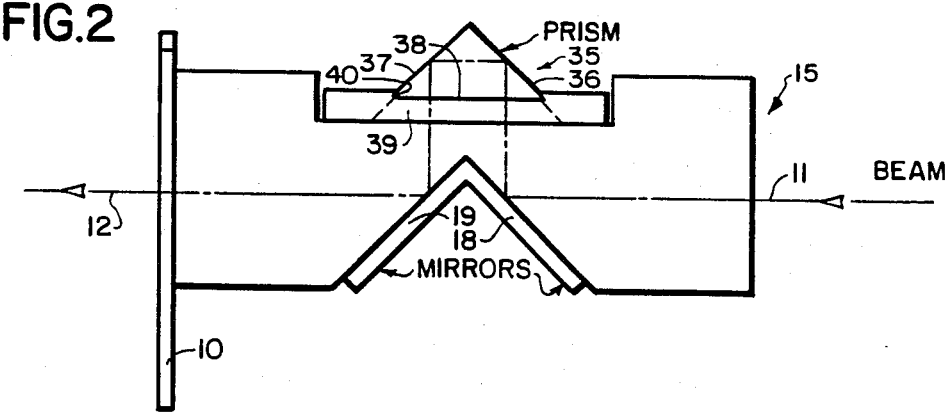
FIGS. 2 and 3 are modifications showing use with differently oriented or shaped prisms.
Figure 3:
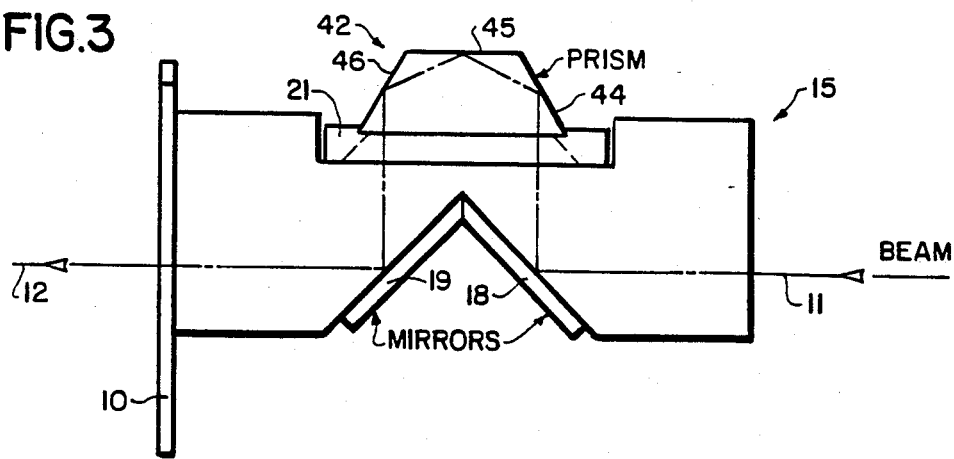

FIGS. 2 and 3 schematically illustrate, respectively, double and triple reflection optical geometries. In these and in subsequent figures, the same reference numerals are employed for the same or similar elements. The FIG. 2 embodiment differs from the FIG. 1 embodiment in that the prism 35 is now inverted, with its apex up, with the result that the beam undergoes two internal reflections on sample surfaces 36 and 37 before returning. Even though a 45° prism is emloyed, the mirrors 18, 19 here have to have a different angular relationship to the beam 11 so it is directed vertically within the block 15, rather than at an angle of 45° as in FIG. 1. Thus the beam enters prism surface 38 orthogonally at one part and exits orthogonally at another part of the same prism surface 38. In addition, the mounting plate opening 39 is configured as a recess rather than with bevelled edges to receive the prism, shown at 40. In FIG. 3, a 60° truncated prism 42 is employed, enabling three internal reflections to occur off of sample surfaces 44, 45 and 46.

Figure 4:
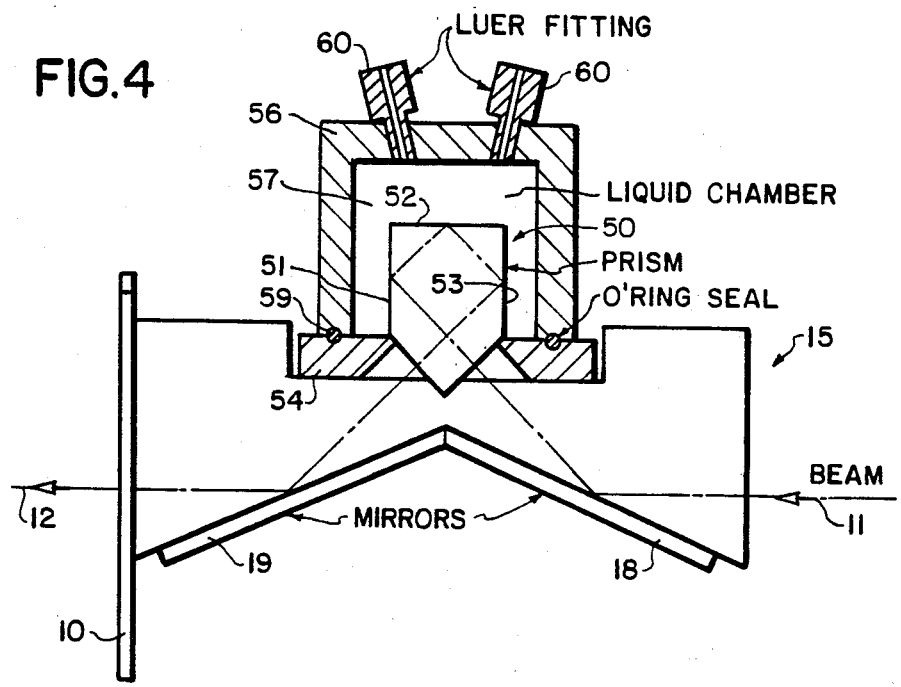
FIG. 4 is a simplified side view of a sealed cell in accordance with the invention.

FIG. 4 illustrates one form of sealed cell employing a pentagonally shaped double pass prism 50 also enabling three internal reflections off of sample surfaces 51, 52 and 53. A mounting plate 54 similar to that used in FIG. 1 is employed here. The figure also illustrates, somewhat schematically, in accordance with the invention, an enclosure 56 mounted on the block 15 for sealing off a chamber or cavity 57 surrounding the sample surfaces 51, 52, 53 of the prism 50 for purposes to be later explained. The enclosure 56 comprises a cover member in the form of a box forming the internal cavity 57. The cover is sealed to the prism support plate 54 by a suitable O-ring seal 59. Luer fittings 60 are provided on top to allow fluid access to the cavity 57.

Figure 5:
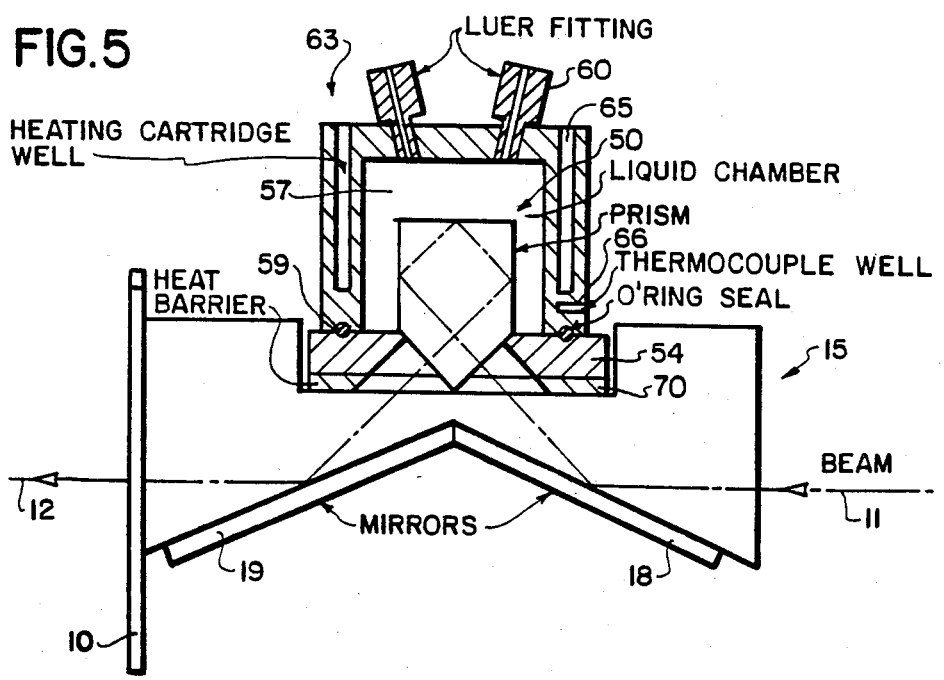
FIG. 5 shows a variation of a sealed cell in accordance with the invention.

FIG. 5 schematically illustrates a modified enclosure 63 incorporating additional features. This embodiment differs from the previous embodiment in that a well 65 is provided in the vertical enclosure walls for receiving an electrical heating cartridge and/or cooling coils (not shown). This allows the sample within the cavity to be heated at an elevated temperature or cooled at a reduced temperature when and if such a measurement is desired. An additional well 66 at the right side wall is configured to receive a thermocouple (not shown) in order to measure and/or to control the sample temperature. In the embodiment, the prism mounting plate is separated by a plate 70 of heat barrier material to heat isolate the sealed cell from the block 15.

FIG. 6 is an exploded view providing more details of a complete sealed cell modified construction in accordance with the invention, employing the 45° triangular prism, with apex down, in the geometry illustrated in FIG. 1. The vertical cell support plate 10, shown at the left, is mounted for vertical movement within an L-shaped stand member 72, comprising a horizontal base plate 73 which supports a vertical member 74 having a rectangular cut-out bounded by slotted walls (not shown) configured to receive the support plate 10. Mounted on the top of the latter by way of an L-shaped bracket 75 is a vertical translation screw 76, the lower screw end 77 of which bears against the top surface 78 of the base plate vertical wall 74, the rear bracket portion 75 being secured, as mentioned, to the top of the cell support plate 10. The horizontal base plate 73 seats in the sampling space of the spectrometer. By rotation of the vertical translation screw 76, the body 15 with attached cell can be translated vertically to align the cell with the incident beam.

In a preferred embodiment, the body or block 15 is hollow and has an inverted U-shaped cross-section, with the entire bottom open, which is closed off by mounting of the two mirrors 18, 19. The block mounting surfaces 16, 17 (FIG. 1) for the mirrors are accurately formed so that mere mounting of the mirrors thereto over the bottom opening, as by a suitable adhesive, accurately positions the mirrors 18, 19 at the correct angle of incidence relative to the beams to direct the beam into and out of the prism 20 at the correct angles. As previously mentioned, the prism mounting surface 27 has a central rectangular opening over which the prism holder plate 21 is mounted. Thus, the beam in its path through the cell passes through air or vacuum and no solids except for the prism IRE itself. Two locating pins 80 are mounted on the bottom recess surface 27 of the block 15, for engaging correspondingly located receiving holes 81 in the prism holder plate 21 for accurate location of the latter. In addition, four alignment screws 82 (only two of which are shown) are located at the four corners of the prism holder plate 21. These alignment screws 82 are preadjusted by the user to accurately orient or align the prism with the beam. This embodiment shows the cell for use with a cover slide 84, that is, a flat glass plate with a holder on top as shown, which is placed over the liquid sample to improve contact with the prism sampling surface and prevent movement of the sample. The O-ring seal 59 in this version extends between the top surface of the cover slide and fits within an annular recess 85 in a cover plate 86. The Luer fittings are shown at 60, by which via an internal channel 87 allows introduction and removal of the fluid sample to the sealed cavity when desired. This subassembly is held together by a yoke member 88 whose opposed ends are configured at 89 to engage projections 90 on the front and rear edges of the prism holder plate 21. See also FIG. 7. At the yoke top, a clamping screw 91 is mounted, whose lower end 92 engages the top of the cover plate 86. By tightening the clamping screw 91, the cavity is readily sealed and the assembly is held tightly together. Loosening of the screw 91 allows disassembly of the cell to clean off the sample or change parts.

FIG. 7 is a partial side view of the yoke mount in the assembled position of the cell. As will be noted, an integral sealed cell subassembly 93, including the prism 20 with sample if present, is created, which subassembly 93 need only be seated in the upper block recess 27 for accurate alignment of the prism 20 with the block mirrors, and the thus-formed assembly is ready for carrying out a measurement.

Figure 8:
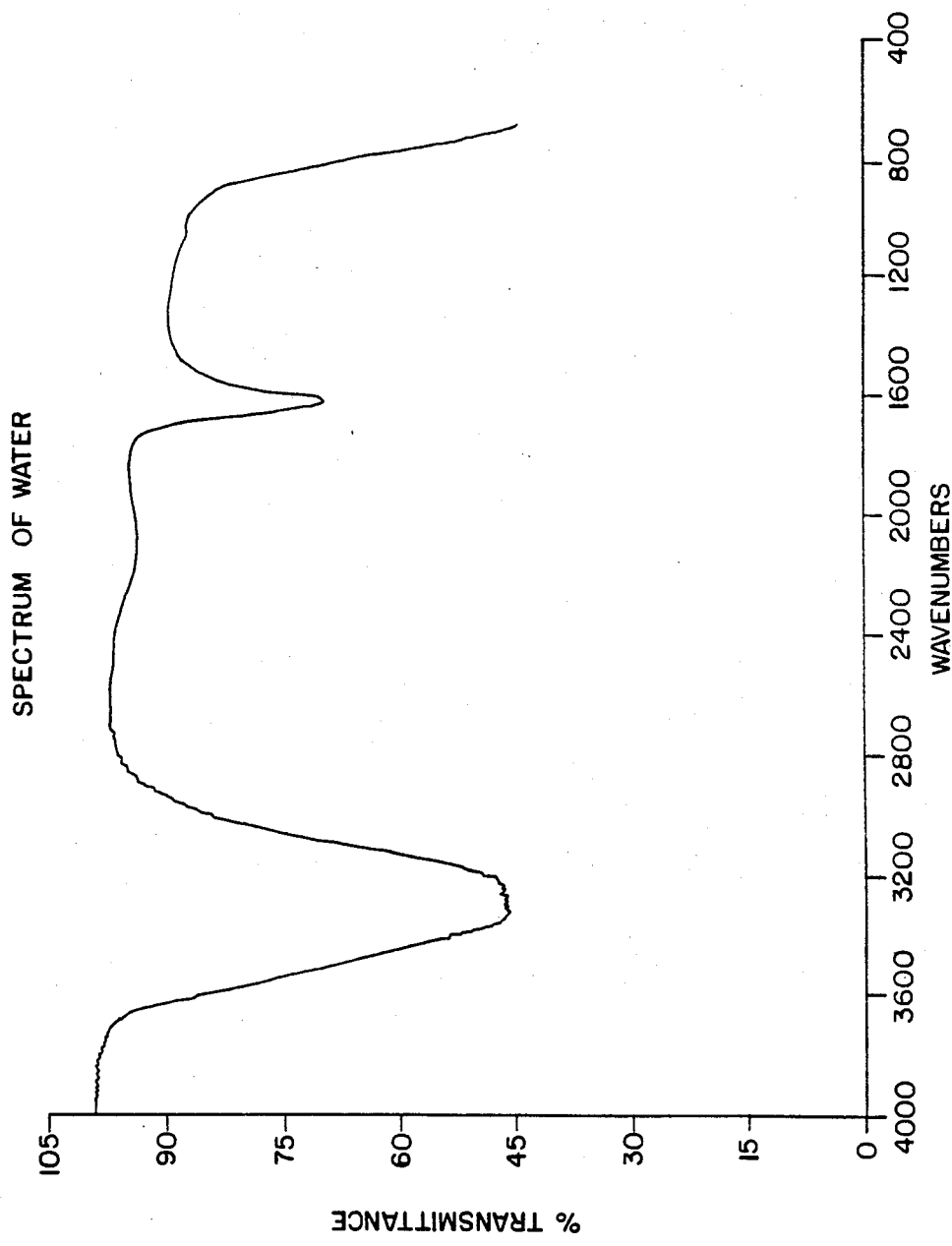
FIG. 8 shows a water spectrum taken with the FIG. 1 embodiment.

The sealed cell accessory described offers many advantages. It not only eliminates the need of amalgamated cells, but it is ideal for highly absorbing solvent samples, for example, aqueous solutions, because the only sample contact is by way of the glass cell cover plate or prism surface. Sample handling is minimized. In its simplest mode, where sealing is unnecessary, the cell can be operated as illustrated in FIG. 1 with the sampling surface exposed (the cover plate and yoke are not present). The liquid sample is simply poured on the exposed prism surface 32, and the spectrum recorded. Afterwards, the prism surface can be wiped dry, ready for another sample. FIG. 8 illustrates the spectrum of water taken with the FIG. 1 embodiment used in this mode, which as will be observed clearly shows the water absorption peaks for infrared radiation using a ZnSe (n=2.4) 45° prism. If desired, the cover slide 84 may be placed over the sample to spread it on the prism surface or avoid rapid evaporation. For volatile samples, vacuum instruments and operation in a flow-thru mode, the sealed cell accessory is used. The cavity 57 dimensions can be maintained very small, of micron dimensions, for low volume samples, or made larger, of millimeter dimensions, for more bulky viscous fluid samples. Spacers 99 placed on the prism surface outside of the O-ring determines the height of the cavity. The light beam does not interact with the seal areas, hence spurious O-ring bands are not introduced. The cover plate 86 may be made of stainless steel, TEFLON or other material to meet the chemical or temperature requirements of the cell. For corrosive samples and high temperatures, the O-ring material can be of KALREZ (a DuPont product), rather than of rubber or other plastics. The Luer fittings allow on-stream analysis by allowing liquids to flow directly through the cavity 57. Since the sampling surfaces are totally unobstructed, the cell is ideal for use as a probe in on-stream analysis. The cover plate 86 can also be used for pressing films or solid samples under pressure against the prism for analysis. The prism cells described without any additional optics may be used in any dispersive or FT instrument.

Instead of ZnSe, other suitable prism materials include CdTe, KRS-5, and diamond for the infrared region, or Ge, Si, or GaAs when higher refractive indices are desired. For the UV-visible range, prism materials such as $Al_2O_3$, diamond, $SrTiO_3$, $TiO_2$, and $ZrO_2$ are suitable. Typical dimensions of the sampling surface for a 45° prism are $\frac{3}{4}"\times 1"$.

While in the embodiments disclosed in FIGS. 4, 5 and 6, the Luer fittings are shown at the top, it will be understood that such location is not critical and they can be located at other suitable places on the cover plate 86 to ensure that the introduced sample by way of pipes connected to the fittings flows past and contacts the sampling surface of the prism 20. For example, one fitting can be provided at or close to the bottom and the other at the top, or the fittings located on opposite sides of the cover plate.

Also, while the disclosed embodiments employ 3-sided, 4-sided or 5-sided prisms for directing the incident radiation to one or more sample surfaces and to redirect the reflected radiation back into the main optics, other prismlike shapes of optical elements well known in the art can be substituted, such as the flat multiple reflection plates illustrated on pages 101 and 104 of my referenced book. If one of the latter is employed, the reflecting mirrors have to be oriented to direct the incident beam into one edge of the plate, and the plate in turn oriented so that the radiation beam exiting from the same or the opposite end is directed in such manner that it can be reoriented by the reflecting mirrors back into coincidence with the optical axis of the system.

In the preferred embodiment disclosed in connection with FIGS. 6 and 7, a single sampling chamber subassembly 93 is mounted on one side of the supporting body 15, with the two mirrors 18, 19 on the opposite side. It will be recognized that if the system were rotated 180° about the optical axis, which would locate the sampling chamber 93 at the bottom, and the mirrors 18, 19 at the top, the system would work identically. It will also be apparent that a supporting body can be suitably configured so as to support two sampling chambers 93, one on top and one on the bottom, and the reflecting mirrors 18, 19 rotatably mounted within the body such that in a first position, the incident radiation beam is directed first, say, to the top sampling chamber, and when rotated 180° to a second position the radiation beam is directed next to the bottom sampling chamber. Thus two successive measurements can be made on the same or different samples within the two independent chambers 93. Similarly, two additional sampling chambers 93 can be mounted on each side of the body, with the rotatable mirrors arranged so that in a third position, rotated 90° from the first or second position, the radiation is directed toward the third sampling chamber on one side and after a 180° rotation to a fourth position next directed toward the fourth sampling chamber on the opposite side. Thus, four successive measurements will be possible on four different samples in the four independent sampling chambers. Thus, my invention is not limited to the use of a single sampling chamber 93 but also embraces the use of multiple sampling chambers with appropriate rotatable or otherwise movable mirror optics for successively directing the radiation beam into selected ones of the sampling chambers. With each sampling chamber connected to a suitable sampling source by way of pipes, on-line measurements of different sample fluids conveyed through each of the sampling chambers becomes possible in a relatively simple and inexpensive manner.

What is claimed is:

1. An internal reflection cell for use in internal reflection spectrometry, comprising:
    (a) a support body transparent to radiation having at a first surface portion an extrance aperture for a radiation beam and having at an opposed second surface portion an exit aperture for a radiation beam,
    (b) a first reflecting means mounted at a third surface portion of the support body and a second reflecting means mounted at a fourth surface portion of the support body adjacent to the third surface portion, said first reflecting means being oriented to receive and reflect an entering radiation beam toward a fifth surface portion of the support body, said fifth surface portion being generally opposed to said third and fourth surface portions,
    (c) an internal reflecting prism having a first surface portion for receiving an allowing entrance of a radiation beam, at least a second surface portion located to receive a sample and upon which the radiation beam internally reflects, and a third surface portion through which the internally-reflected beam can exit from the prism,
    (d) and means for mounting of the prism at the support body fifth surface portion such that its beam entering first surface portion is oriented to receive the beam after reflection from the first reflecting means and to redirect the internally-reflected beam toward the second reflecting means, said second reflecting means being oriented to receive the beam exiting from the prism and redirect it toward the support body exit aperture.

2. An internal reflecting cell as claimed in claim 1, wherein the support body comprises a hollow block-shaped member with the first and second surface portions at opposite block ends, the third and fourth surface portions at the block bottom, and the fifth surface portion at the block top, all of said surface portions surrounding openings in the block whereby the beam in its passage through the block does not pass through any solids with the exception of the prism.

3. An internal reflecting cell as claimed in claim 2, wherein the third and fourth surface portions extend in planes forming an angle optically related to the angle formed by the prism sides, and the fifth surface portion is parallel to the common axis of the incident and exiting beams.

4. An internal reflecting cell as claimed in claim 3, wherein the fifth surface portion contains a recess configured to receive a portion of the prism.

5. An internal reflecting cell as claimed in claim 3 and further including a mounting plate, said mounting plate being configured to seat in a recess at the block fifth surface portion and having a central opening configured to receive and support the prism.

6. An internal reflecting cell as claimed in claim 5, wherein the fifth surface portion has locating pins and the mounting plate has corresponding locating openings for engaging the locating pins, and adjustable means are provided at the plate bottom for adjusting its orientation relative to the beam.

7. An internal reflecting cell as claimed in claim 6 and further including means for removably applying pressure to a sample on the prism's second surface.

8. An internal reflecting cell as claimed in claim 6 and further including means for heating or cooling the cell.

9. An internal reflection sealed cell for use in internal reflection spectrometry, comprising:
(a) a support body transparent to radiation having at a first surface portion an extrance aperture for a radiation beam and having at an opposed second surface portion an exit aperture for a radiation beam,
(b) a first reflecting means mounted at a third surface portion of the support body and a second reflecting means mounted at a fourth surface portion of the support body adjacent to the third surface portion, said first reflecting means being oriented to receive and reflect an entering radiation beam toward a fifth surface portion of the support body, said fifth surface portion being generally opposed to said third and fourth surface portions,
(c) an internal reflecting prism having a first surface portion for receiving and allowing entrance of a radiation beam, at least a second surface portion located to receive a sample and upon which the radiation beam internally reflects, and a third surface portion from which the internally-reflected beam can exit from the prism,
(d) means for mounting of the prism at the support body fifth surface portion such that its beam entering surface is oriented to receive the beam after reflection from the first reflecting means and to redirect the internally-reflected beam toward the second reflecting means, said second reflecting means being oriented to receive the beam exiting from the prism and redirect it toward the support body exit,
(e) and means removably mounted on the support body for sealingly enclosing the prism second surface portion.

10. An internal reflecting cell as claimed in claim 9, wherein the enclosing means comprises a cover means, annular sealing means located between the support body and the cover means, and means for removably locking the cover means to the support body.

11. An internal reflection cell as claimed in claim 10 and further including a mounting means for the prism and configured to accurately mount to the support body, the sealing means is located between the cover means and the prism mounting means, and the locking means is connected between the cover means and the prism mounting means to form an integral unit with the enclosed prism separable from the support body.

12. An internal reflecting cell as claimed in claim 11, wherein the locking means comprises a yoke shaped member having a locking screw engaging the cover and yoke ends configured to removably engage edge portions of the prism mounting means.

13. An internal reflecting cell as claimed in claim 11 and further including a base member and a vertical wall supported thereby, a wall member connected to the support body, and means for adjustably mounting the wall member to the vertical wall for vertically adjusting the height of the support body relative to the base member.

14. An internal reflecting cell as claimed in claim 13 and including Luer fittings mounted on the cover means for flowing a liquid to be analyzed through the cell.

15. An internal reflecting cell as claimed in claim 1, for use with an optical spectrometer in the analysis of liquid samples.

16. An optical subassembly for use with an internal reflection cell in internal reflection spectrometry wherein the cell comprises an entrance aperture for a radiation beam and an exit aperture for the radiation beam, reflecting means to receive and reflect an entering radiation beam toward a cell surface portion and to redirect the returned radiation beam toward the exit aperture; said optical subassembly comprising:
(a) an internal reflecting optical element having a first surface portion for receiving and allowing entrance of a radiation beam, at least a second surface portion located to receive a sample and upon which the radiation beam internally reflects, and a third surface portion from which the internally-reflected beam can exit from the optical element and be returned to the cell,
(b) means for mounting of the optical element at the cell surface portion such that its first beam entering surface is oriented to receive the beam after reflection from the reflecting means and its third surface is oriented to redirect the internally-reflected beam toward the reflecting means,
(c) and means removably connected to the mounting means for sealingly enclosing the optical element second surface portion.

17. An optical subassembly as claimed in claim 16, wherein the enclosing means comprises a cover means, annular sealing means located between the mounting means and the cover means, means for removably locking the cover means to the mounting means, and means for passing fluid samples through the enclosing means.

18. An optical subassembly as claimed in claim 17 and further including means on the mounting means for accurately locating same on the cell.

* * * * *